(12) United States Patent
Stopek et al.

(10) Patent No.: US 8,920,867 B2
(45) Date of Patent: Dec. 30, 2014

(54) METHODS OF FORMING SELF-SUPPORTING FILMS FOR DELIVERY OF THERAPEUTIC AGENTS

(75) Inventors: Joshua Stopek, Guilford, CT (US);
Garrett Ebersole, New Haven, CT (US);
Amin Elachchabi, Hamden, CT (US);
Daniel Broom, Branford, CT (US)

(73) Assignee: Covidien LP, Mansfield, MA (US)

( * ) Notice: Subject to any disclaimer, the term of this patent is extended or adjusted under 35 U.S.C. 154(b) by 14 days.

(21) Appl. No.: 13/239,942

(22) Filed: Sep. 22, 2011

(65) Prior Publication Data
US 2012/0094004 A1    Apr. 19, 2012

Related U.S. Application Data

(60) Provisional application No. 61/394,393, filed on Oct. 19, 2010.

(51) Int. Cl.
| | |
|---|---|
| *A61F 13/00* | (2006.01) |
| *A61L 15/44* | (2006.01) |
| *B05D 3/02* | (2006.01) |
| *B05D 1/36* | (2006.01) |
| *A61K 9/70* | (2006.01) |
| *A61L 31/16* | (2006.01) |
| *A61K 9/00* | (2006.01) |
| *A61K 47/34* | (2006.01) |

(52) U.S. Cl.
CPC ........... *A61K 9/7007* (2013.01); *A61L 31/16* (2013.01); *A61K 9/0024* (2013.01); *A61K 47/34* (2013.01); *A61L 2300/402* (2013.01); *A61L 2300/416* (2013.01)

USPC .......... 427/2.1; 427/2.24; 427/426; 427/2.31; 424/422; 424/443; 424/448

(58) Field of Classification Search
USPC .......... 424/443–445, 447; 427/2.24, 426, 2.31
See application file for complete search history.

(56) References Cited

U.S. PATENT DOCUMENTS

| | | | |
|---|---|---|---|
| 3,887,699 A | 6/1975 | Yolles | |
| 4,767,628 A | 8/1988 | Hutchinson | |
| 5,980,972 A * | 11/1999 | Ding ............................ | 427/2.24 |
| 6,264,702 B1 | 7/2001 | Ory et al. | |
| 6,270,792 B1 | 8/2001 | Guillemet et al. | |
| 6,500,777 B1 | 12/2002 | Wiseman et al. | |
| 7,041,868 B2 | 5/2006 | Greene et al. | |
| 7,060,319 B2 * | 6/2006 | Fredrickson ................. | 427/2.24 |
| 7,175,874 B1 * | 2/2007 | Pacetti ......................... | 427/2.25 |

(Continued)

FOREIGN PATENT DOCUMENTS

| | | |
|---|---|---|
| EP | 2404571 A1 | 1/2012 |
| EP | 2444073 A2 | 4/2012 |

(Continued)

OTHER PUBLICATIONS

European Search Report for EP 11185676.1-1219 date of completion is Aug. 13, 2012 (7 pages).

(Continued)

*Primary Examiner* — Cachet Sellman (57) ABSTRACT

The present disclosure relates to self-supporting films for delivery of a therapeutic agent containing at least one hydrophobic polymer and at least one therapeutic agent. Methods of forming the self-supporting films are also disclosed.

19 Claims, 9 Drawing Sheets

(56) References Cited

U.S. PATENT DOCUMENTS

| | | |
|---|---|---|
| 7,252,837 B2 | 8/2007 | Guo et al. |
| 7,279,177 B2 | 10/2007 | Looney et al. |
| 7,556,598 B2 | 7/2009 | Rao |
| 7,913,371 B2 * | 3/2011 | Klocke et al. .................. 29/453 |
| 2002/0131988 A1 | 9/2002 | Foster et al. |
| 2004/0098118 A1 | 5/2004 | Granada et al. |
| 2004/0220665 A1 * | 11/2004 | Hossainy et al. ............ 623/1.42 |
| 2004/0224007 A1 | 11/2004 | Zhang |
| 2005/0244455 A1 | 11/2005 | Greenawalt |
| 2005/0261782 A1 | 11/2005 | Hoganson |
| 2006/0034887 A1 | 2/2006 | Pelissier |
| 2006/0067983 A1 * | 3/2006 | Swanick et al. .............. 424/434 |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2007/0128343 A1 * | 6/2007 | Chappa .......................... 427/2.1 |
| 2007/0129736 A1 | 6/2007 | Solecki |
| 2007/0198040 A1 | 8/2007 | Buevich et al. |
| 2007/0244548 A1 | 10/2007 | Myers et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0177374 A1 * | 7/2008 | Zheng et al. ................. 623/1.15 |
| 2008/0199506 A1 | 8/2008 | Horres et al. |
| 2009/0036996 A1 | 2/2009 | Roeber |
| 2009/0142385 A1 | 6/2009 | Gross et al. |
| 2009/0163936 A1 | 6/2009 | Yang et al. |
| 2010/0003308 A1 | 1/2010 | Tapolsky et al. |
| 2010/0089409 A1 | 4/2010 | Bertagnoli |
| 2010/0160375 A1 * | 6/2010 | King ............................ 514/315 |

FOREIGN PATENT DOCUMENTS

| | | |
|---|---|---|
| FR | 2 857 851 | 1/2005 |
| WO | 93/11805 | 6/1993 |
| WO | WO 02/34304 | 5/2002 |
| WO | WO 2006/020922 | 2/2006 |
| WO | WO 2006/036967 | 4/2006 |
| WO | WO 2010/093333 A1 | 8/2010 |

OTHER PUBLICATIONS

European Search Report for EP 11185679.5-1219 date of completion is Aug. 13, 2012 (6 pages).

Cohen et al., Dis Colon Rectum Jun. 2005; 48(6): 1130-9. Title: Prevention of Postoperative Abdominal Adhesions by a Novel, Glycerol/Sodium Hyaluronate/Carbonxymethylcellulose-Based Bioresorbable Membrane: A Prospective, Randomized, Evaluator-Blinded Multicenter Study.

European Search Report for EP 11250641.5-2320 (3 pages), Dec. 11, 2011.

K. Kavitha et al., "Design and Evaluation of Transdermal Films of Lornoxicam," International Journal of Pharma and Bio Sciences, Jun. 30, 2011, vol. 2, Issue 2, pp. 54-62.

K. Suknuntha et al., "Properties of Felodipine-poly (vinylpyrrolidone) Solid Dispersion Films and the Impact of Solvents," ScienceAsia, Jun. 30, 2012, vol. 38, No. 2, pp. 188-195.

Search Report issued on Feb. 3, 2014, in corresponding European patent application No. 13188248.2.

* cited by examiner

| | |
|---|---|
| TEST MODE | TENSION |
| PRE-TEST SPEED | 0.17 mm/sec |
| TEST SPEED | 0.17 mm/sec |
| POST-TEST SPEED | 0.17 mm/sec |
| TARGET MODE | DISTANCE |
| DISTANCE | 30.000 mm |
| TRIGGER TYPE | AUTO (FORCE) |
| TRIGGER FORCE | 5.0 g |
| BREAK MODE | RATE |
| BREAK SENSITIVITY | 20.0 g |
| BREAK DEFECT | STOP |
| STOP PLOT AT | TARGET POSITION |
| TARE MODE | AUTO |
| ADVANCED OPTIONS | ON |
| CONTROL OVEN | DISABLED |

FIG. 13

|  | STRESS (N/mm²) | STRAIN (Δl) | MODULUS (MPa) |
|---|---|---|---|
|  | 25 | 2.076923077 | 12.03703704 |
|  | 26 | 1.938461538 | 13.41269841 |
|  | 28 | 2.384615385 | 11.74193548 |
| Average | 26.3333333 | 2.133333333 | 12.39722364 |
| Std Deviation | 1.527525232 | 0.228363529 | 0.891719118 |
| Cross sectional area | 0.1 mm² |  |  |
| Length of dog-bone | 6.5 mm |  |  |

FIG. 14

METHODS OF FORMING SELF-SUPPORTING FILMS FOR DELIVERY OF THERAPEUTIC AGENTS

CROSS-REFERENCE TO RELATED APPLICATION

The present application claims the benefit of and priority to U.S. Provisional Application Ser. No. 61/394,393, filed on Oct. 19, 2010, the entire disclosure of which is incorporated herein by reference.

BACKGROUND

1. Technical Field

The present disclosure describes self-supporting films for delivery of a therapeutic agent, and more particularly, self-supporting films for delivery of a therapeutic agent containing at least one hydrophobic polymer and at least one water-soluble therapeutic agent.

2. Background of Related Art

Delivery of a therapeutic agent through the use of implantable medical devices is described in a wide variety of manners. Existing methods of such delivery of a therapeutic agent predominantly focus on the use of water-soluble drugs and polymers to form thin surface coatings positioned on the surface of the medical device which provide limited therapeutic payloads.

In addition, highly water-soluble drugs may be difficult to formulate for controlled release in that highly water-soluble drugs may offer limited solubility in the organic systems particularly useful with hydrophobic or water-insoluble drug carriers, i.e., hydrophobic polymers. Limited solubility of the highly water-soluble drugs may further lead to poor encapsulation efficiencies of the drug and limited therapeutic payload on the implantable device. Such hydrophilic drugs need a sufficient water barrier to sustain release. Current systems are challenged from a drug payload and sustained release standpoint including offering therapeutic benefits.

It would be beneficial to provide self-supporting films for delivery of a therapeutic agent which does not require the support of a medical device and which displays enhanced therapeutic payload.

SUMMARY

Accordingly, the present disclosure describes methods of forming self-supporting films for delivery of a therapeutic agent. For example, one method of forming a self-supporting film may include providing a first solution which contains at least one hydrophobic polymer and a second solution which contains at least one water-soluble therapeutic agent and passing the first and second solutions through a spray nozzle to generate first droplets of the first solution and second droplets of the second solution. The first and second droplets may be deposited onto an inert substrate and dried to form a single or multilayered self-supporting film.

In some embodiments, a method of forming the self-supporting films described herein may include providing a first solution which contains at least one hydrophobic polymer and a second solution which contains at least one water-soluble therapeutic agent and passing the first solution through a first spray nozzle to generate first droplets of the first solution. The first droplets may be deposited onto an inert substrate to form a first layer. Then the second solution may be passed through a second spray nozzle to generate second droplets of the second solution and depositing the second droplets on the first layer to form a second layer. The first and second layers may be dried to form a multilayer self-supporting film.

In still other embodiments, any number of additional layers may be positioned on top of one another to form the self-supporting multilayer films described herein.

BRIEF DESCRIPTION OF THE DRAWING

These and other characteristics of the present invention will be more fully understood by reference to the following detailed description in conjunction with the attached drawings, in which.

DETAILED DESCRIPTION

The present disclosure describes self-supporting films suitable for delivery of a therapeutic agent. The implantable films include at least one hydrophobic polymer and at least one water-soluble therapeutic agent. The films include a high therapeutic payload of the therapeutic agent and may be single or multi-layered.

By self-supporting, the films described herein display a tensile strength sufficient to maintain a predetermined configuration. For example, in embodiments, the films may form a generally planar configuration displaying a mechanical strength sufficient to maintain the film in the generally planar configuration before, during or after implantation. Although the self-supporting films do not require an additional substrate for support or to maintain the predetermined configuration, it is envisioned that in some embodiments the films described herein may also be combined with any implantable medical device.

In some embodiments, the self-supporting films may display a Young's Modulus ranging from about 500 kPa to about 100 MPa. In other embodiments, the self-supporting films may display a Young's Modulus ranging from about 1 MPa to about 50 MPa. In certain embodiments, the self-supporting films may display a Young's Modulus ranging from about 10 MPa to about 15 MPa.

The thickness of the films may vary depending upon the number of layers in the film and/or the number of 'passes' during the spraying process (described hereinbelow). However, the thickness of the films described herein may on average measure between about 0.1 μm to about 3000 μm. In some embodiments, the thickness of the films may measure between about 1.0 μm to about 1000 μm. In still other embodiments, the thickness of the films may measure between about 10 μm to about 500 μm. Film thickness may influence parameters such as mechanical strength of the multilayer films.

The film thickness may be controlled by factors such as the number of applications of the first and second solutions, the length of time/rate spraying the first and second solutions, polymer solution composition, drug solution composition, flow rate, and use of additives such as viscosity modifiers.

The films described herein may also include a high therapeutic payload consisting of at least one therapeutic agent, especially as compared to other known films of equal thickness. For example, in some embodiments, the therapeutic agent may represent from about 800 μg/cm$^2$ to about 50 mg/cm$^2$. In still other embodiments, the therapeutic agent may represent from about 1 mg/cm$^2$ to about 25 mg/cm$^2$. More specifically, the therapeutic payload of 5-fluorouracil, methotrexate, capsaicin, and bupivacaine hydrochloride, is at least about 800 μg/cm$^2$ and up to about 50 mg/cm$^2$. In other embodiments, different therapeutic agents may be present in different amounts.

Unlike films formed by solvent casting, the self-supporting films described herein are not limited by the solubility of the water-soluble agent and/or the hydrophobic polymer in a common solvent. Rather, the polymer and agent of the self-supporting films may not share a common solvent and thus the water-soluble therapeutic agent is not limited in solubility by the hydrophobic polymer. For example, the self-supporting films may be formed using at least two solutions, wherein the hydrophobic polymer forms a first solution in a first solvent and the water-soluble therapeutic agent forms a second solution in a second solvent.

Further, it is believed that spraying films on a medical device (e.g., mesh) compared to other conventional methods, such as dip coating, provides increased loading of the therapeutic agent. As demonstrated in FIG. 8, the saturation and payload limits for dip coating bupivacaine hydrochloride (HCl) in a solution (in water) is 5% w/v (weight/volume) versus dip coating bupivacaine HCl solution (in MeOH) is 12% w/v.

Figure 8:
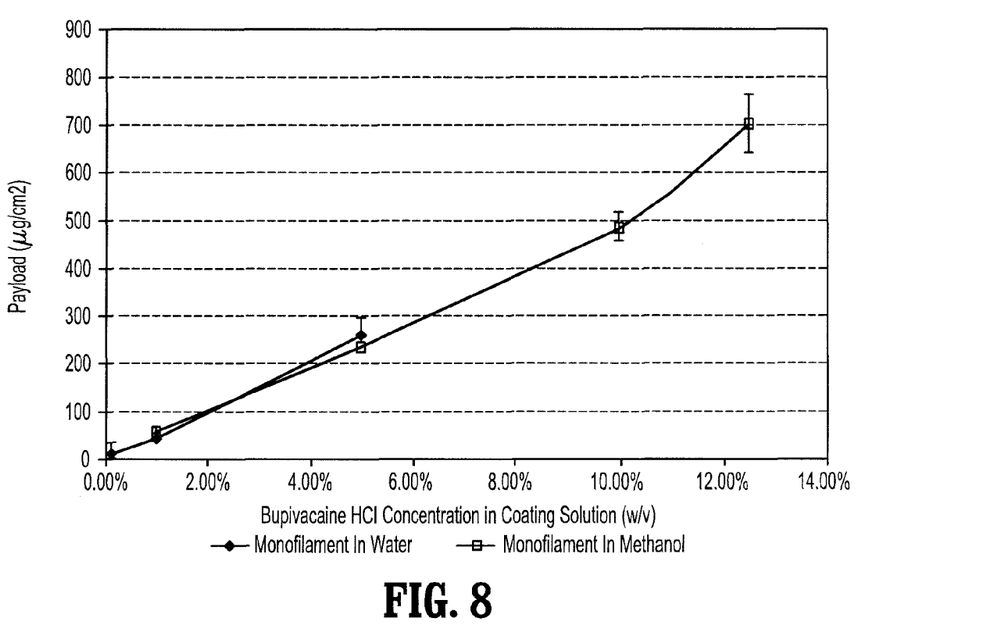
FIG. 8 is a graph illustrating a comparison to therapeutic payload on a medical device via dip-coating.

More particularly FIG. 8 illustrates the loading limits for a polyester mesh (Parietex™ monofilament mesh) without a polymer film.

Figure 9:
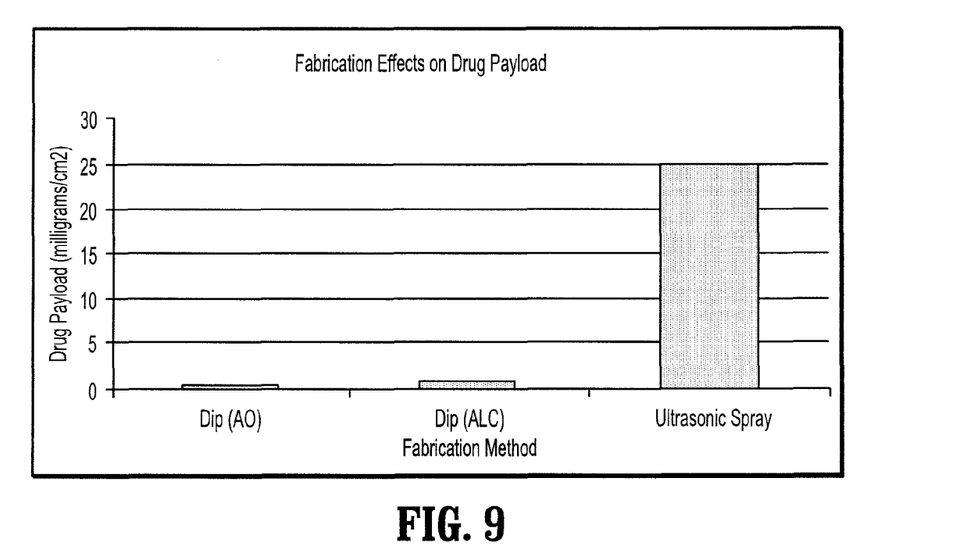
FIG. 9 is a graph illustrating a comparison to therapeutic payload on a medical device via dip-coating and spray-coating.

FIG. 9 illustrates data presented in FIG. 8, coating a mesh with bupivacaine HCl utilizing a dip coating method, compared to films which have been ultrasonically sprayed as described in Example 5 (PS35-1, PS30-4). The payload limits for the dip coated mesh, AQ (Aqueous, e.g., water) and ALC (Alcohol, e.g., MeOH) do not exceed 1 mg/cm$^2$. Conversely, films created using ultrasonic spraying as described herein, can be configured to load up at least about 25 mg/cm$^2$. Drug loading created through ultrasonic spraying of films on mesh, unlike drug loading via dip coating mesh, meets the clinical target payload of >300 mg.

The films ability to include a high therapeutic payload of the therapeutic agent may be a result of the unique manner in which the self-supporting films may be formed. For example, a self-supporting film as described herein may be fabricated by passing a first solution containing the hydrophobic polymer and a second solution containing the therapeutic agent through an ultrasonic spray nozzle to form droplets. The droplets may be mixed while falling towards or being deposited onto an inert substrate, such as a silicone sheet. After drying, the film may be separated from the inert substrate.

Films of the present disclosure may comprise continuous or discontinuous films. For example, a continuous film such as those shown in FIGS. 2 and 4A include a single, uninterrupted layer. In another embodiment, films or layers of films may be discontinuous, as illustrated in FIG. 5 (later described). Individual layers of the multilayer films may be continuous or discontinuous.

Figure 10:
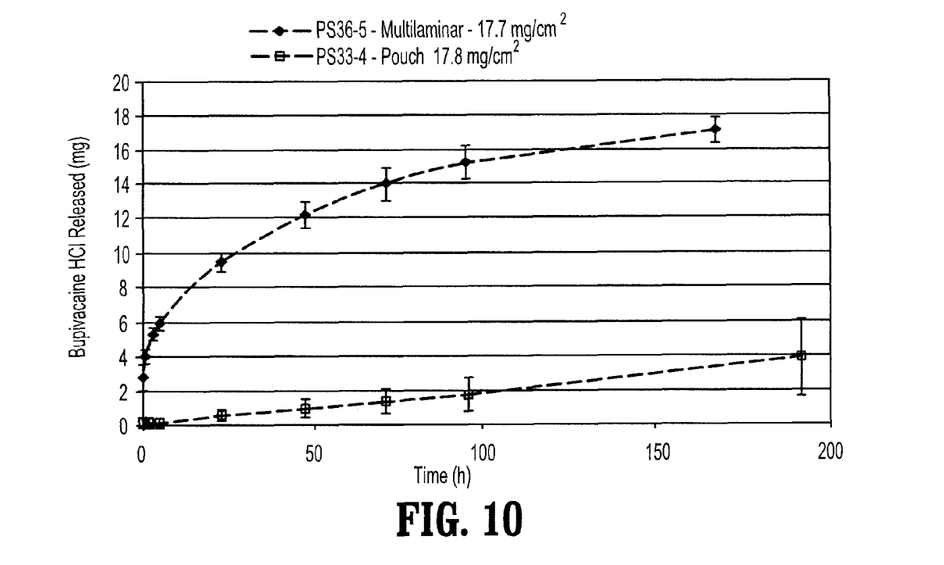
FIG. 10 is a graph illustrating a comparison of the therapeutic release of bupivacaine HCL from multilaminar and pouch configured medical devices.

Additionally, the film's construct may control parameters such as drug release and diffusion. In some embodiments the layer containing the therapeutic agent extends to the edge of the multilayer film (See FIG. 4A), in yet alternate embodiments, the layer containing the therapeutic agent does not extend to the edge of the multilayer film, referred to herein as a pouch configuration (See FIG. 4B). Release rates may vary depending on the whether or not the therapeutic agent is present at the edge of the multilayer film. FIG. 10, illustrates on exemplary embodiment in which the bupivacaine HCl release is slowed down utilizing a pouch configuration. The multilaminar configuration has been formulated to include about 17.7 mg/cm$^2$ of bupivacaine HCl, and the pouch configuration has been formulated to include about 17.8 mg/cm$^2$ of bupivacaine HCl. Example 7 described herein provides additional info with regards to processing parameters, etc. It should be understood that if the below data was extracted for a longer period of time, total release for the two configurations would be approximately similar.

Film thickness may also play a role in the drug release and diffusion. For example, it has been shown that as film thickness increases, the rate of release for the therapeutic agent decreases or slows down over time.

Figure 11:
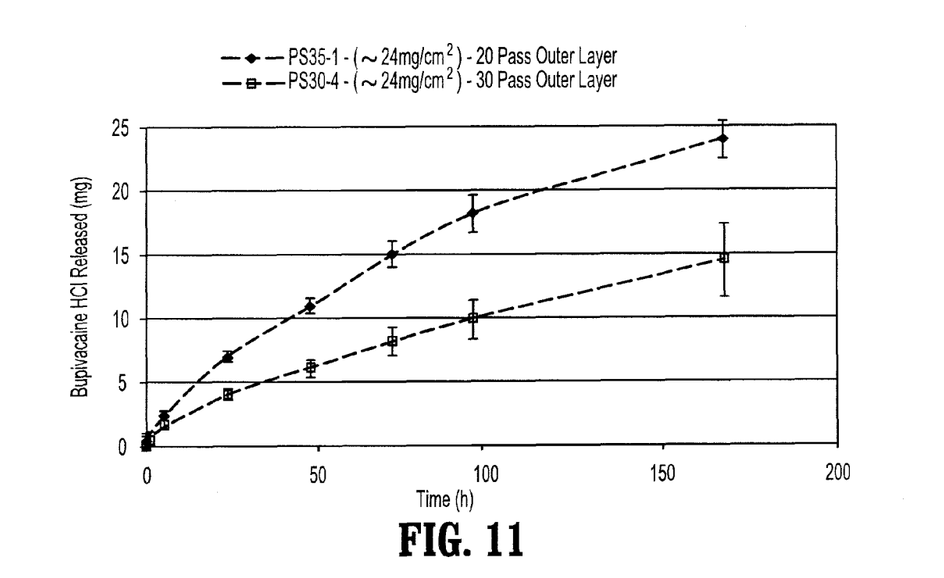
FIG. 11 is a graph illustrating a comparison of the therapeutic release of bupivacaine HCL from films of varying thicknesses.

The films created in FIG. 11 are described in greater detail in Example 5. Thicker films (e.g., with increased number of passes), have a slower release rate, compared with thinner films. Both films above have been formulated to include about 24 mg/cm$^2$ of bupivacaine HCl. It should be understood that if the above data was extracted for a longer time point, total release for the different configurations would be approximately similar.

Figure 12:
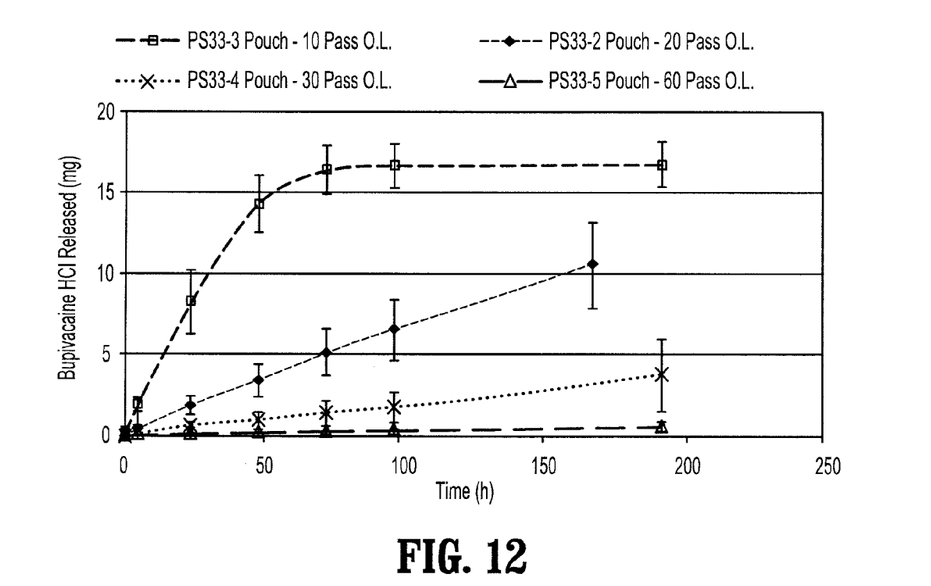
FIG. 12 is a graph illustrating a comparison of the therapeutic release of bupivacaine HCL from films formed from various oases of the sprayer.
Figure 13:
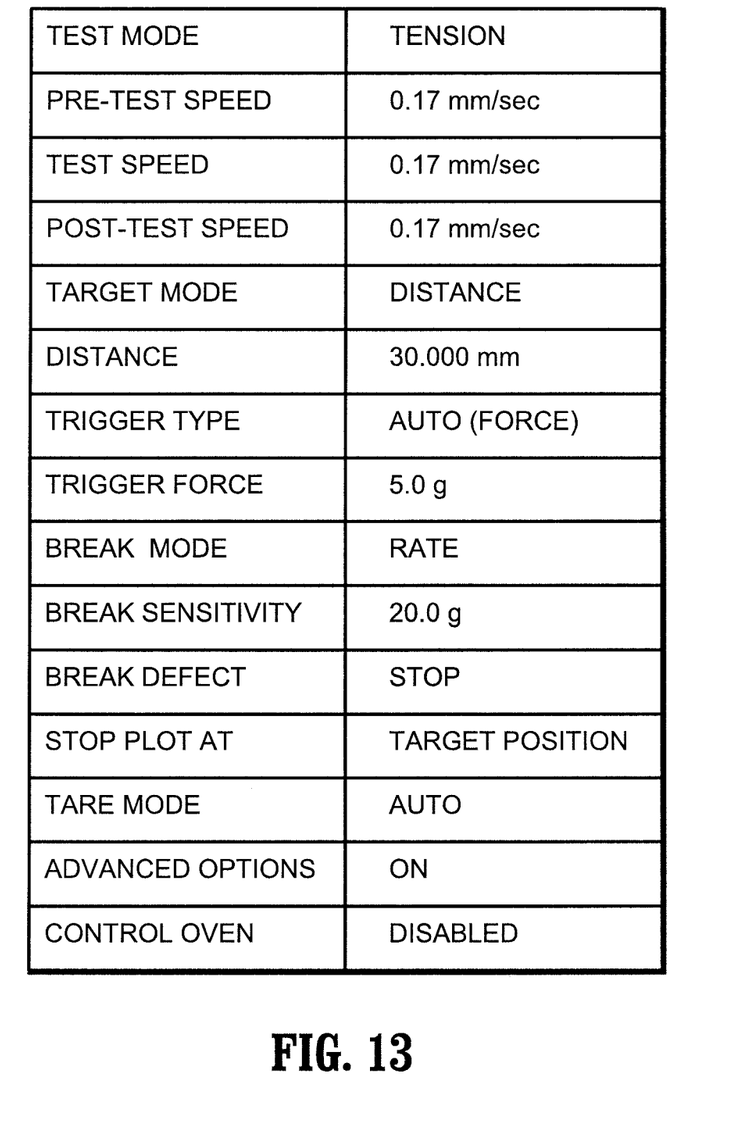
FIG. 13 is a graph illustrating the parameters used to test the strength of films formed as described in Example 1.
Figure 14:
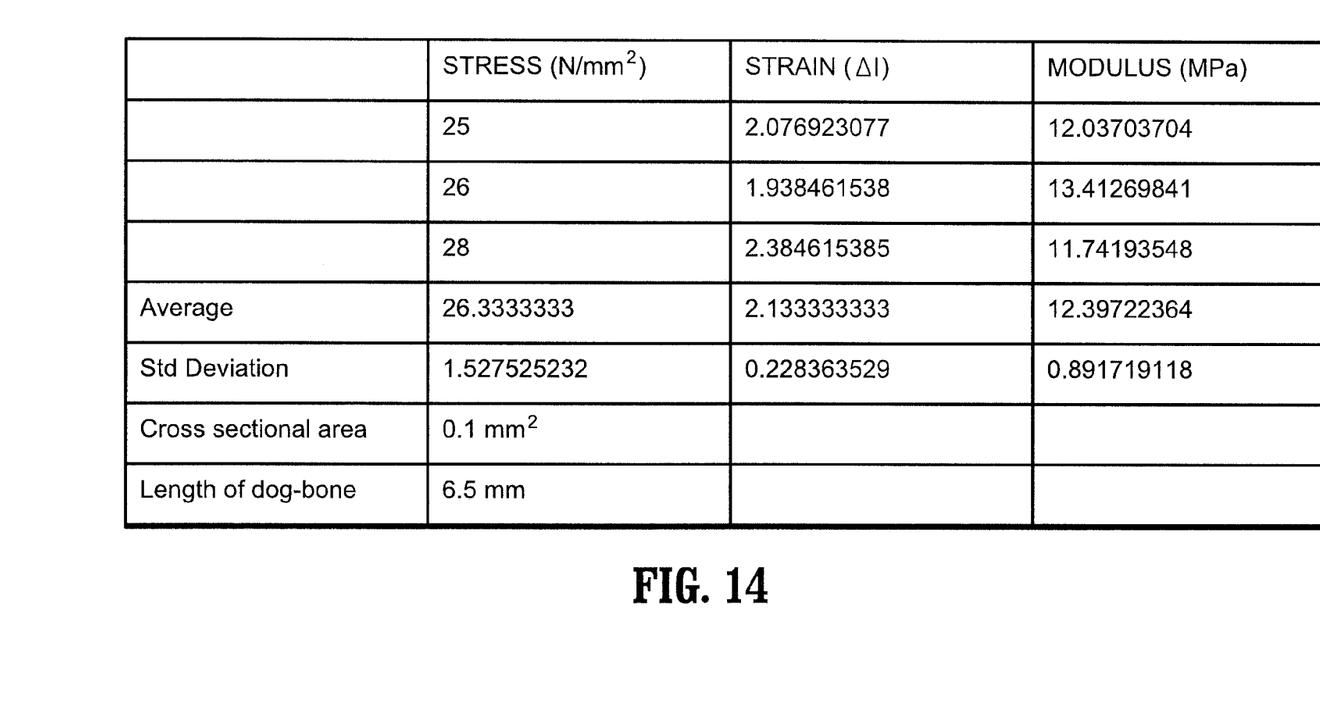
FIG. 14 is a graph illustrating the results of the strength of the films formed as described in Example 1 and tested as described in Example 8.

Similarly, for closed-edge samples, increasing the film thickness and/or changing the number of passes per layer alters the release rate of the therapeutic agent. FIG. 12 below illustrates how increasing the number of passes in each outer layer, changes the release profile and release rate. The release rate slows down as the number on passes in the outer layers increase. Samples shown below are exemplary embodiments and depending on rate of release and total release desired, the parameters may be altered to change total release and release rate. It should be understood that if the below data was extracted for a longer time point, total release for the different configurations would be approximately similar. Example 6 described herein provides additional information with regards to processing parameters, etc.

In some embodiments, the films include a single layer containing a hydrophobic polymer and a therapeutic agent. A multilayered film may be created by stacking or combining several layers of films containing the hydrophilic polymer and therapeutic agent. In other embodiments, the multilayered films include a first layer containing a hydrophobic polymer and a second layer containing a therapeutic agent. It may be useful to have an exposed layer of a therapeutic agent for providing unidirectional drug delivery.

In other embodiments, the films include a tri-layer structure wherein a third layer containing a therapeutic agent, is positioned between a first layer containing a hydrophobic polymer and a second layer containing the same or a different hydrophobic polymer. The third layer may comprise a hydrophobic polymer and a therapeutic agent, whereas the first and second layer may comprise only a hydrophobic polymer. For example, the first and second layers may comprise a copolymer of about 10 weight % glycolide and about 90 weight % ε-caprolactone; while the third layer comprises a copolymer of about 10 weight % glycolide and about 90 weight % ε-caprolactone in combination with bupivacaine hydrochloride.

The tri-layer structure, similar to a sandwich-type structure, may be combined with other films including other single, double, and/or other tri-layer structures. As previously discussed, any of the multilayer films disclosed herein may be combined with mesh. It should be noted that multiple layers may utilize similar or different polymers depending on the intended use as well as drug release profiles. Further, thicker and thinner layers may be created through process variation.

The films may include any hydrophobic polymer suitable for implantation and capable of displaying sufficient mechanical strength to be considered. Certain layers may also include hydrophilic polymers. Some non-limiting examples of suitable absorbable polymers which may be utilized in accordance with the present disclosure include or may be derived from at least one of the following materials: aliphatic polyesters; polyamides; polyamines; polyalkylene oxalates; poly(anhydrides); polyamidoesters; copoly(etheresters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly(bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-,L- and meso lactide); glycolide (including glycolic acid); å-caprolactone, p-dioxanone (1,4-dioxan-2-one); trimethylene carbonate (1,3-dioxan-2-one); alkyl derivatives of trimethylene carbonate; Ä-valerolactone; ã-butyrolactone; ã-butyrolactone; å-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; á, á diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers which may be utilized in accordance with the present invention include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In certain embodiments, the hydrophilic polymers may comprise the first, second and third layers. A copolymer of 10 wt % glycolide and 90 wt % ε-caprolactone may be utilized to form the first, second and third layers.

In embodiments, the hydrophobic polymers may include homopolymers or copolymers which include lactide, glycolide, dioxanone, trimethylene carbonate, and ε-caprolactone. For example, the therapeutic agents described herein may be combined with copolymers, i.e., random, or block copolymers, of lactide and glycolide or glycolide and ε-caprolactone. Increasing the amount of glycolide may increase the films degradation rate. While increasing the amount of lactide and/or caprolactone may extend the degradation/absorption profile of the film. For example, lactide rich copolymers, i.e., greater than about 50% lactide, may be particularly useful to enhance a particular polymer's solubility, such as glycolide. In particular embodiments, a copolymer of 10 wt % glycolide and 90 wt % ε-caprolactone may be utilized.

The hydrophobic polymers may form polymer solutions, including suspensions, emulsions, dispersions and the like, prior to being passed through an ultrasonic sprayer. Some non-limiting examples of solvents suitable for forming the polymer solutions may include methylene chloride, chloroform, N-methylpyrrolidone, tetrahydrofuran, dimethylformamide, methanol, ethanol, hexanes, acetone and combinations thereof. The polymer may represent from about 1.0% to about 25% (w/w) in the solution.

In particular embodiments, the solvent used to the polymer solution may not be the same solvent used to form the therapeutic agent solution. The therapeutic agent may not be miscible in the solvent used to form the polymer solution. In addition, the polymeric solutions and/or the therapeutic solutions may include at least one optional ingredient such as emulsifiers, viscosity enhancers, dyes, pigments, fragrances, pH modifiers, wetting agents, plasticizers, antioxidants, foaming agents, amphiphilic compounds, and the like. For instance, the solutions may include a foaming agent to induce porosity of the film. In another example, the solutions may include amphiphilic compounds to increase water diffusion of the film. The optional ingredients may represent up to about 10% (w/w) of the polymer solution.

Tissue reactive chemistries may also be added to the multilayered films of the present disclosure. Suitable tissue reactive chemistries include, for example, reactive silicones, isocyanates, N-hydroxy succinimides ("NHS"), cyanoacrylates, aldehydes (e.g., formaldehydes, glutaraldehydes, glyceraldehydes, and dialdehydes), and genipin. As used herein, succinimides also include sulfosuccinimides, succinimide esters and sulfosuccinimide esters, including N-hydroxysuccinimide ("NHS"), N-hydroxysulfosuccinimide ("SNHS"), N-hydroxyethoxylated succinimide ("ENHS"), N-hydroxysuccinimide acrylate, succinimidyl glutarate, n-hydroxysuccinimide hydroxybutyrate, combinations thereof, and the like.

The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic affect, such as, anti-adhesives, anti-microbials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the films described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present self-supporting films include, lidocaine, bupivacaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

The water-soluble drug may not need to be converted to a salt form, i.e., tetracycline hydrochloride. In some embodiments, the therapeutic agent may include an anesthetic, i.e., bupivacaine, lidocaine, benzocaine, and the like.

The multilayer films described herein may be used in treating cancers not limited to those such as breast cancer, lung cancer, esophageal cancer, gastric cancer, colon cancer, stomach cancer, and brain cancer. Suitable water-soluble therapeutic agents which may be used in treating cancer include, but are not limited to 5-fluorouracil, methotrexate, cisplatin, daunorubucub, mitoxantrone, and carboplatin.

The multilayer films described herein may also be used in treating post-operative pain. Post-operative pain may be commonly associated with procedures such as inguinal and ventral hernia repair, hysterectomy, thoracotomy, coronary artery bypass, hemorrhoidectomy, adhesiolysis, breast reconstruction, spine surgery, and joint repair/replacement. Suitable water-soluble therapeutic agents which may be used in treating post-operative pain include, but are not limited to lidocaine hydrochloride, mepivacaine hydrochloride, bupivacaine hydrochloride, and capsaicin. Therapeutic payloads for these water-soluble drugs are described herein.

In particular embodiments, multilayer films may comprise a copolymer of 10 weight % glycolide and 90 weight % ε-caprolactone in combination with a therapeutic agent such as bupivacaine hydrochloride, capsaicin, or 5-fluorouracil.

The water-soluble therapeutic agents may be combined with any suitable solvent to form a therapeutic solution. Some useful non-limiting examples include organic solvents such as methylene chloride, chloroform, N-methylpyrrolidone, tetrahydrofuran, dimethylformamide, methanol, ethanol, hexanes, acetone, water and combinations thereof. In some embodiments, the solvent for the therapeutic agent is not a co-solvent for the hydrophobic polymer. In some embodiments, the hydrophobic polymer is not miscible in the solvent for the therapeutic agent.

The water-soluble therapeutic agent may form a solution at a concentration ranging from about 1 microgram/mL to about 1 gram/mL. In certain embodiments, the concentration of the therapeutic solution may range from about 1 mg/mL to about 500 mg/mL. In still other embodiments, the concentration of the therapeutic solution may range from about 10 mg/mL to about 300 mg/mL. By solution, the therapeutic preparation is intended to include suspensions, emulsions, dispersions, and the like.

The therapeutic solution and the polymer solution may be passed through an ultrasonic spray nozzle to form the self-supporting films described herein. Ultrasonic sprayers include ultrasonic spray nozzles which may be used to generate vibrations leading to atomization of the solutions. The sprayer body consists of three principal sections: front horn, the atomizing section; rear horn, the rear section, and a section consisting of a pair of disc-shaped piezoelectric transducers. Working in unison, these three elements provide means for creating the vibration required to atomize the solutions delivered to the nozzle surface. The solutions enter through a fitting on the rear, passes through the tube and then the central axis of the front horn. Finally, the solution reaches the atomizing surface of the nozzle where atomization takes place. Piezoelectric transducers convert electrical energy provided by an external power source into high-frequency mechanical motion or vibration. The solution absorbs the underlying vibration energy and generates capillary waves. When the amplitude of the capillary waves exceeds a critical value, the waves collapse ejecting small droplets of the solutions.

The ultrasonic sprayer nozzle may include a variety of controls which may be adjusted to alter the characteristics of the self-supporting films described herein. Some non-limiting examples include: vibration frequency, operational power; solution flow rates, nozzle speed, and length of movement of the nozzle. In forming the films described herein, the sprayer nozzle may vibrate at a frequency ranging from about 20 kHz to about 100 kHz and may operate at a power ranging from about 2 to 10 watts. In some embodiments, the sprayer nozzle may vibrate at a frequency of about 48 kHz and operate at a power of about 6 watts.

In certain embodiments, the ultrasonic spray nozzles may be movable. The nozzle may move a speed ranging from about 10 mm/sec to about 200 mm/sec. In other embodiments, the nozzle speed may range from about 50 mm/sec to about 150 mm/sec. In addition, the height of the movable nozzles may range from about 30 mm to about 60 mm from the inert substrate.

Also, the flow rate of the solutions passed through the sprayer nozzle may vary within the range of about 0.1 mL/min to about 5 mL/min. In embodiments, the flow rate of the solutions may be within the range of about 0.5 mL/min and 2.0 mL/min. The flow rate may be different for each of the polymer solution and the therapeutic solutions. It is envisioned that each of the sprayer controls may be individually adjusted for each of the different solutions being passed therethrough.

Multilayer films of the present disclosure may be sprayed onto an inert substrate which may include a release liner substrate utilized for fabrication only. The inert substrate may be separated from the film prior to packaging or conversely, the substrate may be packaged with the film and removed prior to implantation. In other embodiments, a mesh may be positioned on an inert substrate, and the multilayer film may be sprayed directly onto mesh, creating a multilayer composite film. In other embodiments, the inert substrate is part of the implantable therapeutic multilayer composite film.

In yet alternate embodiments, the mesh may be provided with a film backing, such as collagen. The multilayer film may be directly sprayed onto the collagen film backing, which then may be subsequently combined with a mesh, creating a multilayer film composite. For example, the polymer film containing a multilayer film may be combined with a mesh using methods discussed hereinbelow.

Films may be dried at ambient (25° C.) or elevated temperatures and humidity. Depending on film thickness/number of layers, the films may dry in from about 1 minute to about 24 hours.

Multilayer films of the present disclosure may be combined with meshes described herein using methods including but not limited to adhesives, glues, solvent welding, spot welding, solvent casting, melt pressing, heat staking, and the like. In other embodiments, the multilayer film may be formed directly on the mesh.

Figure 1:
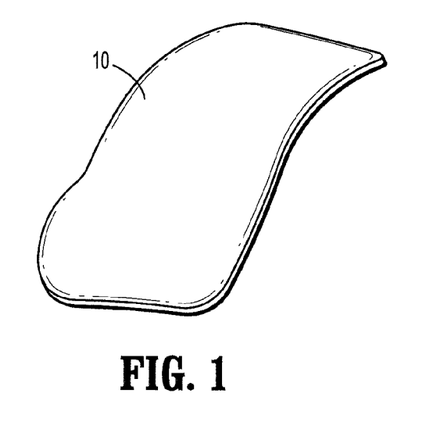
FIG. 1 is a diagrammatic illustration of a barrier layer realized as a self-supporting film, according to one embodiment described in the present disclosure.

Turning now to FIG. 1 which illustrates self-supporting film 10 wherein the hydrophobic polymer and the therapeutic agent are contained in a single layer. Although film 10 is self-supporting, film 10 maintains flexibility to the extent it can be handled without tearing prior to implantation and can adjust to various amounts of force when implanted.

Figure 2A:
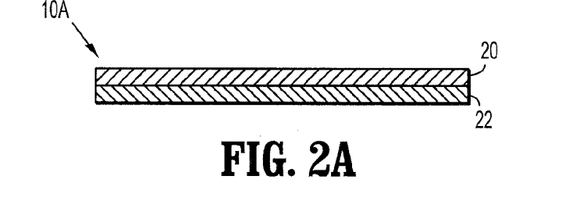
FIGS. 2A, 2B, and 2C are cross-sectional views of the self-supporting film in accordance with embodiments described in the present disclosure.
Figure 2B:
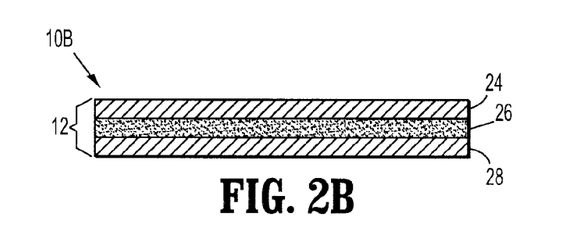
Figure 2C:
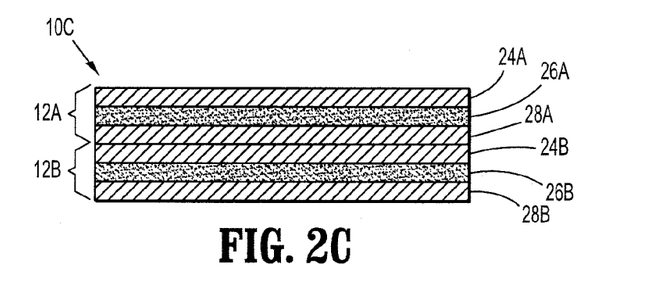
Figures 3A, 3B:
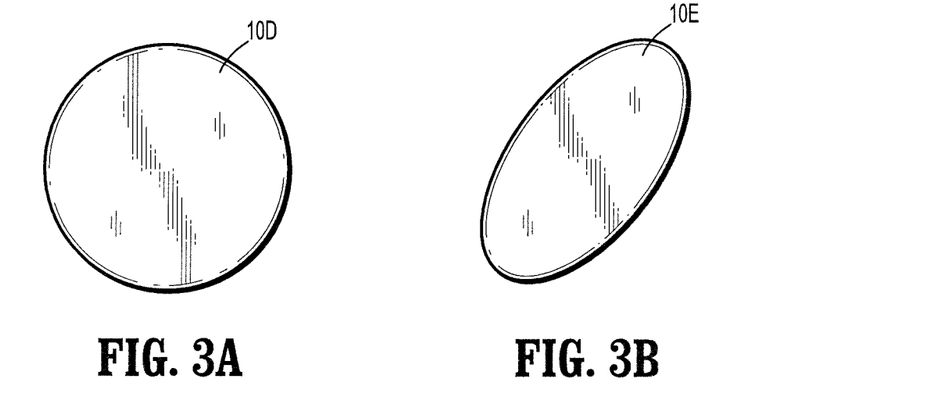
FIGS. 3A, 3B, 3C, 3D, 3E, and 3F are diagrammatic views of the self-supporting films in accordance with other embodiments described in the present disclosure.
Figure 3C:
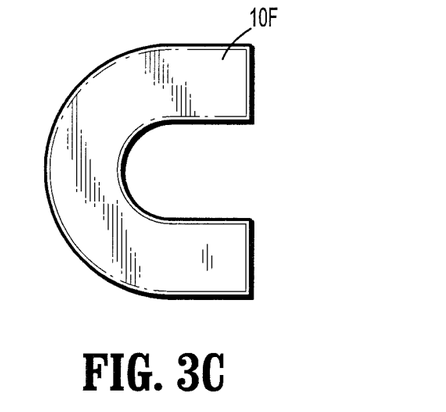
Figure 3D:
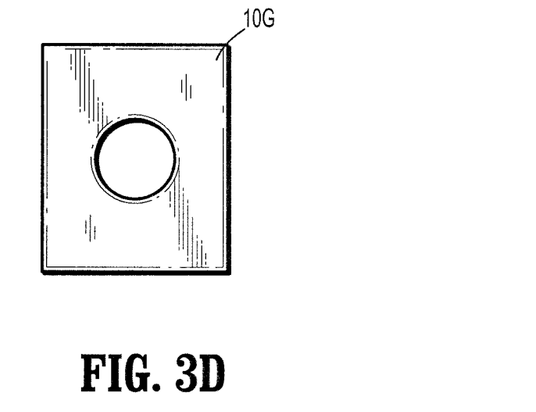
Figure 3E:
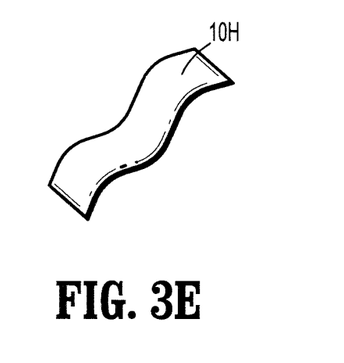
Figure 3F:
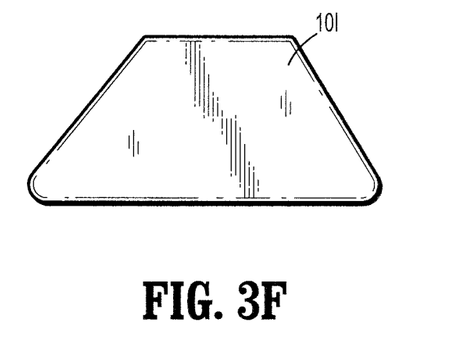

FIGS. 2A, 2B, and 2C illustrate side views of self-supporting multilayer films. For example, in FIG. 2A, film 10A is shown including first layer 20 and second layer 22. First layer 20 includes at least one hydrophobic polymer and second layer 22 includes at least one water-soluble therapeutic agent. In some embodiments, the therapeutic agent and/or the hydrophobic polymer may be combined in either first layer 20 or second layer 22.

FIG. 2B shows multilayer film 10B displaying tri-layer structure 12 including first layer 24, second layer 26, and third layer 28 with the therapeutic agent positioned between two polymer layers. First layer 24 may include at least one hydrophobic polymer and second layer 26 may include at least one water-soluble therapeutic agent. Third layer 28 may include the same or different hydrophobic polymer as included in first layer 24. For example, in some embodiments, second layer 26 may include a therapeutic agent, such as bupivacaine, and the first and third layers may include the same hydrophobic polymer material, i.e., poly(glycolide-co-caprolactone). In another example, all three layers may include the same polymer material, i.e., poly(glycolide-co-caprolactone) and second layer 26 may also include a highly water-soluble therapeutic agent, i.e., bupivacaine.

FIG. 2C illustrates two tri-layer structure 12A and 12B as shown in FIG. 2B stacked on top of each other to form multilayer film 10C. First tri-layer structure 12A includes first layer 24A, second layer 26A, and third layer 28A with the therapeutic agent positioned in second layer 26A between the two polymer layers, first and third layers 24A and 28A. Second tri-layer structure 12B includes fourth layer 24B, fifth layer 26B, and sixth layer 28B with the therapeutic agent positioned in fifth layer 26B between the two polymer layers, fourth and sixth layers 24A and 28A. Although shown as a sandwich-like structure in FIG. 2B, tri-layer structures 12A and 12B may include any conceivable combination of the polymer materials and therapeutic agents described herein.

When stacked, film 10C may include increased payload of the therapeutic agent without compromising mechanical properties. It is envisioned that more than two tri-layer structures 12 may be stacked on top of each other to form the self-supporting films. In embodiments, 2 to about 25 of the tri-layer structure may be stacked on top of each other to form the self-supporting film.

Also, the thickness of each of the individual layers in the multilayer films may control the release of the therapeutic agent from the film. For example, increasing the thickness of only the polymer layer may decrease the rate at which the therapeutic agent may be released into the surrounding tissue following implantation. Conversely, decreasing the thickness of only the polymer layer may increase the rate at which the therapeutic agent may be released.

FIGS. 3A through 3F show additional embodiments or configurations of the self-supporting films 10. The embodiments include self-supporting film 10D in a circular configuration, self-supporting film 10E in an oval configuration, self-supporting film 10F in a U-bend configuration, self-supporting film 10G in a square configuration having a circular aperture, self-supporting film 10H in a wave configuration, and self-supporting film 10I in an irregular shape configuration. Each of the configurations of self-supporting film 10D through 10I represents different types of configurations. The configurations illustrated are by no means the only possible configurations for self-supporting film 10. One of ordinary skill in the art will appreciate that the specific shape or configuration of self-supporting film 10 can vary as desired and that the shapes and configurations depicted in FIG. 1 and FIGS. 3A through 3F are illustrative of only a small number of possible shapes and configuration.

Figure 4A:
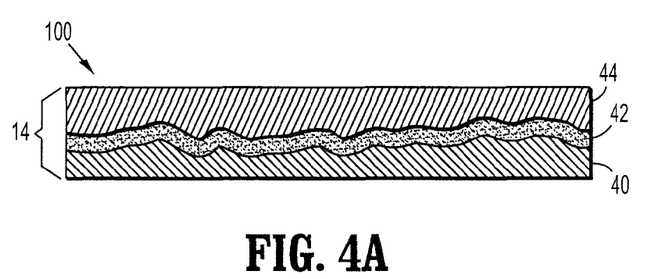
FIG. 4A is a cross-sectional view of a self-supporting film in accordance with yet another embodiment described in the present disclosure.
Figure 4B:
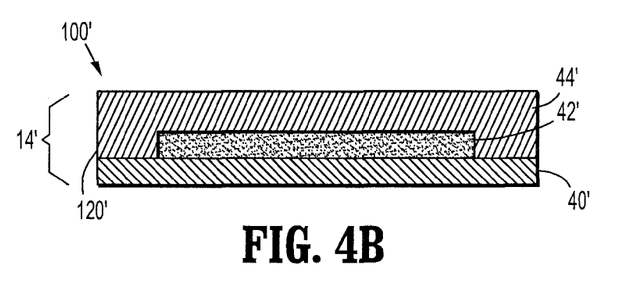
FIG. 4B is a cross-sectional view of a self-supporting film in accordance with yet another embodiment described in the present disclosure.
Figure 5:
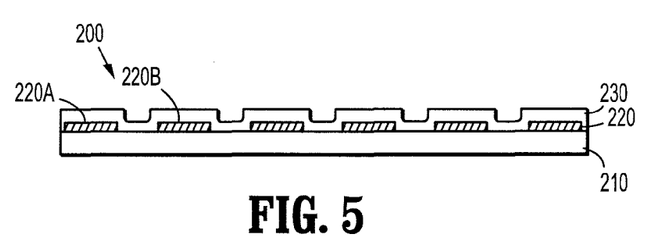
FIG. 5 is a cross-sectional view of a self-supporting film in accordance with the present disclosure, the film having a discontinuous layer.

As shown in FIGS. 4A-4B, the multilayer film 100 displays a tri-layer structure 14 including a first layer 40, third layer 44, and second layer 42 disposed therebetween the first and third layer. The second layer comprises a water-soluble therapeutic agent and a hydrophobic polymer, while the first and third layers each comprise a hydrophobic polymer. The hydrophobic polymers may be the same or different in each layer. However, unlike the multiple layers shown in FIGS. 2A-2C, the topography of each of the three layers 40, 42, and 44 may be different throughout the length of the film. Because the films may be formed using an ultrasonic sprayer nozzle, the film layers may be formed from a plurality of droplets which, in some embodiments, may be deposited onto the inert substrate in any random amount.

Figure 4C:
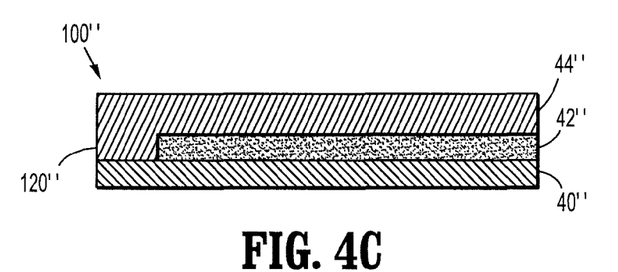
FIG. 4C is a cross-sectional view of a self-supporting film in accordance with yet another embodiment described in the present disclosure.

It will be understood that FIGS. 4B and 4C are similar embodiments to FIG. 4A and therefore all numerals and descriptions which are the same are designated with the prime marks and the differences will be described below. The multilayer film includes a tri-layer structure 14', however the second, middle layer 42' does not extend to the outer edge 120' of the film. Rather, at least one of first layer 40', and third layer 44' are positioned along outer edge 120' and covering second layer 42'. By controlling the distance of the second layer (containing the therapeutic agent) to the outer edge 120' the release of the therapeutic agent may be altered/controlled.

In certain embodiments, as shown in FIG. 4B, at least one of first layer 40' and third layer 44' may cover second layer 42' along the entire length of outer edge 120'. In other embodiments, at least one of first layer 40" and third layer 44" may cover second layer 42" along only intermittent portions of the length of outer edge 120" to create intermittent portions along outer edge 120" wherein second layer 42" is not covered, as shown in FIG. 4C.

An alternate embodiment of a tri-layer film having a discontinuous layer is illustrated in FIG. 5. The multilayer film 200 includes a first, continuous layer 210; a third, continuous layer 230; and a second discontinuous layer 220, disposed therebetween. The discontinuous layer may be created through using a screen or a template or using a pre-programmed spray pattern. Although the discontinuous layer is illustrated as the second layer, it should be understood that the discontinuous layer may comprise any of the layers of the multilayer film. The discontinuous layer 220 may include the same or different polymers and/or therapeutic agents. For example, the discontinuous layer 220 may include a first copolymer and a first therapeutic agent comprising 220a, while a second copolymer and a second, different therapeutic agent may comprise 220b.

In certain embodiments, meshes may be combined with multilayer films of the present disclosure to create a multilayer film composite. The mesh includes a first surface and a second surface. At least one of the first surface or the second surface of the mesh may be positioned adjacent at least one of the first or third layers of the multilayer film. In alternate embodiments, the mesh may be positioned between various layers of the multilayer film. For example, the mesh may be positioned between the first and second layer of the multilayer film.

Figure 6:
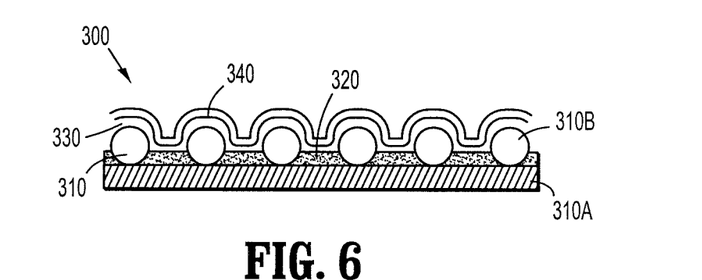
FIG. 6 is a cross-sectional view of a self-supporting film composite in accordance with the present disclosure.

FIG. 6 illustrates a multilayer film composite in accordance with the present disclosure. The multilayer composite 300, includes collagen backed mesh 310, such as Parietex™ Composite Mesh (PCO) having multilayer film according to the present disclosure. The mesh structure 310b includes a collagen film 310a on a first surface thereof. The multilayer film disposed on the PCO mesh includes a first, discontinuous layer 320, a second continuous layer 330 and a third, continuous layer 340. As illustrated, the first layer 320 is disposed directly on the collagen film, between the fibers of the mesh 310b. The discontinuous layer 320 may be created using methods described above. The second layer 330 is deposited on mesh 310b and the first layer 320. The third layer 340 is subsequently deposited on the second layer 330.

Figure 7:
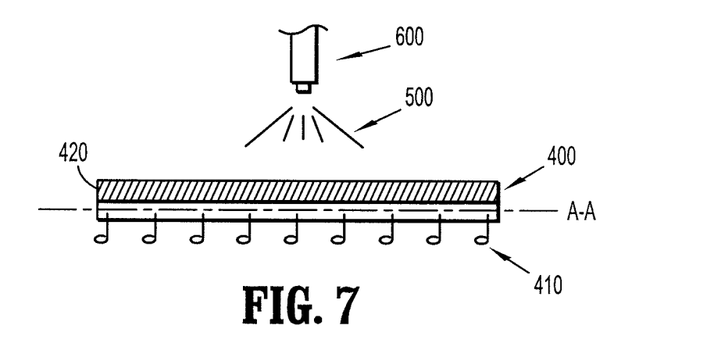
FIG. 7 is a cross-sectional view illustrating one example of how self-supporting films according to the present are formed.

FIG. 7 schematically illustrates the process of spray coating Parietex Progrip™ self-fixating mesh 400. The mesh 400 includes grip members 410 projecting from a first surface of the mesh 400. The grip members extend generally perpendicular to a longitudinal axis A-A of the mesh 400. The mesh 400 also includes a collagen backing 420 positioned on a second surface of the mesh 400. As illustrated a sprayer 600 is dispensing a solution 500 onto the surface of the collagen backing. The sprayer 600 may continue to dispense solution 500 until the multilayer film has been created.

Example 1

A first polymer solution and a second therapeutic solution are provided. The first polymer solution contains 30 mg/mL poly(glycolide-co-caprolactone) dissolved in methylene chloride. The second therapeutic solution contains 100 mg/mL of bupivacaine dissolved in methanol.

Both solutions are fed into an ultrasonic sprayer and passed through at least one ultrasonic spray nozzle. The two solutions are kept separate from each other until atomized at the tip of the nozzle. The nozzle vibrates at a frequency of 48 kHz and is operated at 6 watts. The solutions are passed through the nozzle at a flow rate of about 1 mL/min while the nozzle is moving at a rate of 100 mm/sec at heights ranging from 30 mm to 60 mm.

The atomized solutions form droplets that mix when the droplets fall from the tip of the nozzle onto an inert sheet of silicone. An air curtain kept at a pressure of 1.0 kPa surrounds the falling droplets.

The droplets deposited onto the silicone sheet are dried and then separated from the silicone sheet. The self-supporting films are then sterilized and packaged.

Example 2

A first polymer solution and a second therapeutic solution are provided. The first polymer solution contains 3% poly (glycolide-co-caprolactone) dissolved in methylene chloride. The second therapeutic solution contains 100 mg/mL of bupivacaine dissolved in methanol.

The first and second solutions are fed into an ultrasonic sprayer and passed through a first and second ultrasonic spray nozzle, respectively. The nozzle vibrates at a frequency of 48 kHz and is operated at 6 watts. The solutions are passed through the nozzles at a flow rate of about 1 mL/min while the nozzle is moving at a rate of 100 mm/sec at heights ranging from 30 mm to 60 mm. An air curtain kept at a pressure of 1.0 kPa surrounds the falling droplets.

The first polymer solution is passed through the first spray nozzle to form droplets that are deposited onto the silicone sheet to form a first polymer layer. The thickness of the polymer layer may be controlled by the number of applications of the coating solution.

Then the first polymer solution and the second therapeutic solution are passed through the first and second spray nozzles, respectively, to form droplets which mix when the droplets fall from the tip of the nozzle onto the first polymer layer previously formed on the sheet of silicone. This forms a second layer which includes both the polymer and therapeutic agent.

Then the first polymer solution is passed through the first spray nozzle again while the flow rate of the second therapeutic solution is stopped. Droplets of the first polymer solution are formed and deposited onto the second layer previously formed on top of the first layer on the silicone sheet to form a tri-layer structure.

The tri-layer structure is then exposed to increased heat and compression to dry and join the tri-layer structure. The film is subsequently combined with a mesh using an adhesive to create a multilayer composite. The multilayer composite is then sterilized and packaged.

Example 3

A first polymer film and a second polymer film is formed containing poly(glycolide-co-caprolactone). The first polymer film is positioned on a silicone sheet beneath an ultrasonic sprayer nozzle.

A therapeutic solution is formed containing 100 mg/mL of bupivacaine dissolved in methanol. The therapeutic solutions is fed into the ultrasonic sprayer and passed through an ultrasonic sprayer nozzle to form droplets that are deposited onto the preformed first polymer film to form an intermediate therapeutic layer.

The second polymer film is positioned on the intermediate therapeutic layer to form a tri-layer structure. The tri-layer structure is sprayed with a binding agent to bind the three layers together. The tri-layer structure is then exposed to heat and/or compression to complete the binding process.

Example 4

A first polymer solution and a second therapeutic solution are provided. The first polymer solution contains 3% w/v poly(glycolide-co-caprolactone) dissolved in methylene chloride. The second therapeutic solution contains 50 mg/mL of bupivacaine dissolved in ethanol.

The first and second solutions are fed into an ultrasonic sprayer and passed through a first and second ultrasonic spray nozzle, respectively. The nozzle vibrates at a frequency of 48 kHz and is operated at 6 watts. The solutions are passed through the nozzles at a flow rate of about 1 mL/min while the nozzle is moving at a rate of 100 mm/sec at heights ranging from 30 mm to 60 mm. An air curtain kept at a pressure of 1.0 kPa surrounds the falling droplets.

The first polymer solution is passed through the first spray nozzle to form droplets that are deposited onto a collagen film to create a first polymer layer. The thickness of the polymer layer may be controlled by the number of applications of the coating solution.

Then the first polymer solution and the second therapeutic solution are passed through the first and second spray nozzles, respectively, to form droplets which mix when the droplets fall from the tip of the nozzle onto the first polymer layer previously formed on the collagen film. This forms a second layer which includes both the polymer and therapeutic agent.

Then the first polymer solution is passed through the first spray nozzle again while the flow rate of the second therapeutic solution is stopped. Droplets of the first polymer solution are formed and deposited onto the second layer previously formed on top of the first layer on the collagen film to form a tri-layer structure.

The tri-layer structure is then combined with a mesh and subsequently exposed to increased heat and compression to dry and join the tri-layer structure to the mesh. The multilayer composite is then sterilized and packaged.

Example 5

A first polymer solution and a second polymer solution are provided. The first polymer solution contains 30 mg/mL poly (glycolide-co-caprolactone) dissolved in dichloromethane. The second polymer solution contains 30 mg/mL of bupivacaine and 30 mg/mL poly(glycolide-co-caprolactone) dissolved in dichloromethane and methanol (7:3 ratio).

The first and second solutions are fed into an ultrasonic sprayer and passed through an ultrasonic spray nozzle. The nozzle vibrates at a frequency of 48 kHz and is operated at 6 watts. The solutions are passed through the nozzles at a flow rate of about 2 mL/min while the nozzle is moving at a rate of 100 mm/sec at a height of 30 mm. A nitrogen curtain kept at a pressure of 1.0 kPa surrounds the falling droplets.

The first polymer solution is passed through the first spray nozzle to form droplets that are deposited onto a collagen sheet to form a first, outer polymer layer. The thickness of the polymer layer may be controlled by the number of applications/passes of the coating solution. Films in this example either included 20 or 30 passes as the first, outer polymer layer.

Then the second therapeutic solution is passed through the spray nozzles, to form droplets which fall from the tip of the nozzle onto the first polymer layer previously formed on the sheet of silicone. This forms a second layer which includes both the polymer and therapeutic agent. The second layer included about 125 passes.

Then the first polymer solution is passed through the spray nozzle again, creating a third, outer polymer layer. Droplets of the first polymer solution are formed and deposited onto the second layer previously formed on top of the first layer on the collagen sheet. The third outer layer also included 20 or 30 passes. A tri-layer structure is created having a first outer layer, a second layer, and a third outer layer, with a therapeutic drug loading of about 24 mg/mL.

The films were then soaked in Phosphate buffered saline (PBS) for up to 200 hours to determine drug release. Those results are shown in FIG. 11.

Example 6

A first polymer solution and a second polymer solution are provided. The first polymer solution contains 30 mg/mL poly (glycolide-co-caprolactone) dissolved in dichloromethane. The second polymer solution contains 50 mg/mL of bupivacaine hydrochloride and 30 mg/mL poly(glycolide-co-caprolactone) dissolved in dichloromethane and methanol (1:1 ratio).

The first and second solutions are fed into an ultrasonic sprayer and passed through an ultrasonic spray nozzle. The nozzle vibrates at a frequency of 48 kHz and is operated at 6 watts. The solutions are passed through the nozzles at a flow rate of about 2 mL/min while the nozzle is moving at a rate of 100 mm/sec at a height of 30 mm. A nitrogen curtain kept at a pressure of 1.0 kPa surrounds the falling droplets.

The first polymer solution is passed through the first spray nozzle to form droplets that are deposited onto a collagen sheet to form a first, outer polymer layer. The thickness of the polymer layer may be controlled by the number of applications/passes of the coating solution. Films in this example include 10, 20, 30, or 60 passes as the first, outer polymer layer.

A masking template is placed over the first, outer polymer layer. Then the second therapeutic and polymer solution are passed through the spray nozzle, to form droplets that fall from the tip of the nozzle onto the first polymer layer previously formed on the sheet of silicone. This forms a second layer which includes both the polymer and therapeutic agent. The second layer included about 75 passes.

The masking template is removed. Then the first polymer solution is passed through the first spray nozzle again while the flow rate of the second therapeutic solution is stopped, creating a third, outer polymer layer. Droplets of the first polymer solution are formed and deposited onto the second layer previously formed on top of the first layer on the collagen sheet. The third outer layer also included 10, 20, 30, or 60 passes. A tri-layer structure is created having a first outer layer, a second layer, and a third outer layer.

The films were then soaked in PBS for up to 200 hours to determine drug release. Those results are shown in FIG. 12.

Example 7

A first polymer solution and a second polymer solution are provided. The first polymer solution contains 30 mg/mL poly (glycolide-co-caprolactone) dissolved in dichloromethane. The second polymer solution contains 30 mg/mL of bupivacaine and 50 mg/mL poly(glycolide-co-caprolactone) dissolved in dichloromethane and methanol (1:1 ratio).

The first and second solutions are fed into an ultrasonic sprayer and passed through an ultrasonic spray nozzle. The nozzle vibrates at a frequency of 48 kHz and is operated at 6 watts. The solutions are passed through the nozzles at a flow rate of about 2 mL/min while the nozzle is moving at a rate of 100 mm/sec at a height of 30 mm. A nitrogen curtain kept at a pressure of 1.0 kPa surrounds the falling droplets.

The first polymer solution is passed through the first spray nozzle to form droplets that are deposited onto a collagen sheet to form a first, outer polymer layer. The thickness of the polymer layer may be controlled by the number of applications/passes of the coating solution. Films in this example included 30 passes as the first, outer polymer layers.

Then the second therapeutic solution is passed through the spray nozzles, to form droplets which fall from the tip of the nozzle onto the first polymer layer previously formed on the sheet of silicone. This forms a second layer which includes both the polymer and therapeutic agent. The second layer included about 75 passes.

Then the first polymer solution is passed through the spray nozzle again, creating a third, outer polymer layer. Droplets of the first polymer solution are formed and deposited onto the second layer previously formed on top of the first layer on the collagen sheet. The third outer layer also included 30 passes. A tri-layer structure is created having a first outer layer, a second middle layer, and a third outer layer. The films illustrated in FIG. 10, PS33-4, and PS 36-5 have been formulated to include 17.8 and 17.7 mg/cm$^2$ of bupivacaine hydrochloride, respectively.

The films were then soaked in PBS for up to 200 hours to determine drug release. Those results are shown in FIG. 10.

Example 8

A sheet of film made as described in Example 1 was cut into dog-bone shaped structures. The dog-bone structures were then individually fixed onto a tensile loading clamp on a TA XT-Plus Analyzer according to the data in FIG. 13. The clamp applied a constant force on the dog-bone structure and recorded the forces until the dog-bone structures breaking point. The Young's modulus was then calculated by using a stress/strain relationship based on the dimensions of the dog-bone structure. Results are shown in FIG. 14.

It will be understood that various modifications may be made to the embodiments disclosed herein. Therefore, the above description should not be construed as limiting, but merely as exemplifications within the scope and spirit of the claims appended hereto.

What is claimed is:

1. A method of forming a film for delivery of a therapeutic agent comprising:

passing a first solution containing at least one hydrophobic polymer and a chlorinated solvent, and a second solution containing at least one water-soluble therapeutic agent and a second solvent that is different from the chlorinated solvent through a spray nozzle to generate first droplets of the first solution and second droplets of the second solution such that solubility of the at least one water-soluble therapeutic agent is not limited by the at least one hydrophobic polymer;

depositing the first and second droplets on an inert fabrication substrate to form at least one layer;

drying the first and second droplets to form an implantable self-supporting film; and separating the implantable self-supporting film from the inert fabrication substrate prior to implantation, wherein the implantable self-supporting film displays a Young's Modulus of about 500 kPa to about 100 MPa and the therapeutic agent represents from about 800 μg/cm$^2$ to about 50 mg/cm$^2$ of the implantable self-supporting film.

2. The method of claim 1 wherein the first solution comprises at least one hydrophobic polymer selected from the group consisting of aliphatic polyesters, polyhydroxyalkanoates, polyothroesters, polyurethanes, polyanhydrides, polymer drugs and combinations thereof.

3. The method of claim 2 wherein the aliphatic polyesters is selected from the group consisting of lactide, glycolide, trimethylene carbonate, alkyl derivatives of trimethylene carbonate, Δ-valerolactone, β-butyrolactone, γ-butyrolactone, ε-decalactone, hydroxybutyrate, hydroxyvalerate, 1,4-dioxepan-2-one, 1,5-dioxepan-2-one, 6,6-dimtheyl-1,4-dioxan-2-one, 2,5-diketomorpholine, pivalactone, α,α-diethylpropiolactone, ethyl carbonate, ethylene oxalate, 3-methyl-1,4-dioxane-2,5-dione, 3,3-diethyl-1,4-dioxan-2,5-dione, 6,8-dioxabicycloctane-7-one, homopolymers, copolymers, and combinations thereof.

4. The method of claim 1 wherein the first solution comprises a copolymer of about 10 weight percent glycolide and about 90 weight percent ε-caprolactone.

5. The method of claim 1 wherein the chlorinated solvent is selected from the group consisting of methylene chloride, chloroform, dichloromethane, and combinations thereof.

6. The method of claim 1 wherein the second solution comprises at least one water-soluble therapeutic agent selected from the group consisting of antimicrobial agents, anesthetics, analgesics, anticancer agents, angiogenic agents, fibrotic agents, antimitotics, chelating agents, peptides, proteins, DNA, RNA, nucleotides, liposomes, blood products, hormones, water-soluble silver salts, growth factors, antibodies, interleukins, cytokines, and combinations thereof.

7. The method of claim 1 wherein the second solution comprises at least one water-soluble therapeutic agent selected from the group consisting of bupivacaine hydrochloride, fluorouracil, cisplatin, methotrexate, capsaicin and combinations thereof.

8. The method of claim 1 wherein the second solvent is selected from the group consisting of methanol, ethanol, water, saline, isopropanol, acetic acid and combinations thereof.

9. The method of claim 1 wherein the spray nozzle comprises at least one ultrasonic spray nozzle.

10. The method of claim 9 wherein the spray nozzle further comprises operating at a power ranging from about 2 to about 10 watts.

11. The method of claim 9 wherein the spray nozzle further comprises operating at a power of about 6 watts.

12. The method of claim 9 wherein the spray nozzle further comprises moving at a rate ranging from about 10 mm/sec to about 200 mm/sec.

13. The method of claim 9 wherein the spray nozzle further comprises moving at a rate of about 50 mm/sec to about 150 mm/sec.

14. The method of claim 1 wherein passing the first and second solutions through a spray nozzle further comprises a flow rate ranging from 0.5 mL/min to about 2 mL/min.

15. The method of claim 1 wherein the spray nozzle further comprises vibrating at a frequency ranging from about 20 kHz to about 100 kHz.

16. The method of claim 1 wherein the spray nozzle further comprises vibrating at a frequency of about 48 kHz.

17. The method of claim 1 wherein depositing the first and second droplets includes forming a single layer.

18. The method of claim 1 wherein depositing the first and second droplets includes forming at least two layers.

19. The method of claim 1, further comprising attaching the implantable self-supporting film to a medical device selected from the group consisting of a film, a mesh, a scaffold, a buttress, a pledget, and a foam.

* * * * *